(12) United States Patent
Ikeuchi et al.

(10) Patent No.: US 8,883,687 B2
(45) Date of Patent: Nov. 11, 2014

(54) HERBICIDAL COMPOSITION

(75) Inventors: Toshihiro Ikeuchi, Tokyo (JP); Tetsuo Ohkawa, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/344,878

(22) Filed: Jan. 6, 2012

(65) Prior Publication Data
US 2012/0100992 A1   Apr. 26, 2012

Related U.S. Application Data

(62) Division of application No. 11/887,623, filed as application No. PCT/JP2006/313471 on Jul. 6, 2006, now Pat. No. 8,114,815.

(30) Foreign Application Priority Data

Jul. 8, 2005   (JP) .................... 2005-200793
Jan. 5, 2006   (JP) .................... 2006-000945

(51) Int. Cl.
  *A01N 43/54*   (2006.01)

(52) U.S. Cl.
  CPC ..................... *A01N 43/54* (2013.01)
  USPC .......................................... 504/243

(58) Field of Classification Search
  None
  See application file for complete search history.

(56) References Cited

U.S. PATENT DOCUMENTS

| | | | |
|---|---|---|---|
| 3,681,045 A | | 8/1972 | Gough |
| 4,936,901 A | * | 6/1990 | Surgant et al. ............. 504/133 |
| 5,164,126 A | * | 11/1992 | Kalishek et al. ............. 264/4.7 |
| 6,458,748 B1 | | 10/2002 | Yoshimura et al. |
| 7,160,841 B2 | | 1/2007 | Fujita et al. |
| 2004/0011262 A1 | * | 1/2004 | Fujita et al. ..................... 111/130 |
| 2009/0053272 A1 | | 2/2009 | Wagenblast |

FOREIGN PATENT DOCUMENTS

| | | |
|---|---|---|
| JP | 09-249505 | 9/1997 |
| JP | 2000-044546 | 2/2000 |
| JP | 2002-179507 | 6/2002 |

OTHER PUBLICATIONS

JP 09-249505, machine translation.*
International Search Report issued Sep. 26, 2006 in International (PCT) Application No. PCT/JP2006/313471.

* cited by examiner

*Primary Examiner* — Sue Liu
*Assistant Examiner* — Thor Nielsen
(74) *Attorney, Agent, or Firm* — Wenderoth, Lind & Ponack, LLP

(57) ABSTRACT

Provided is a herbicidal composition comprising a herbicidally active compound selected from a difluoromethanesulfonylanilide compound represented by the general formula (I):

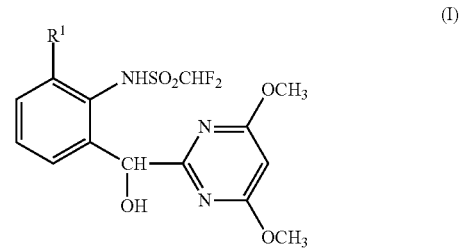

(I)

wherein $R^1$ represents a hydrogen atom, an alkyl group or an alkoxyalkyl group; or a salt thereof encapsulated in a microcapsule, or a herbicidal composition comprising the herbicidally active compound encapsulated in a microcapsule and a benzoic acid compound represented by the general formula (II):

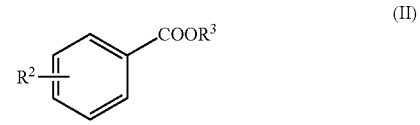

(II)

wherein $R^2$ represents a hydrogen atom, an alkyl group having 1 to 15 carbon atoms, a hydroxyl group, a nitro group, or an amino group; and $R^3$ represents a hydrogen atom, an alkali metal atom or an alkyl group. The herbicidal composition exert a pharmacological effect for a prolonged period of time, can alleviate or prevent any harmful effect and can reduce the environmental load.

2 Claims, No Drawings

HERBICIDAL COMPOSITION

This application is a Divisional of U.S. application Ser. No. 11/887,623, filed Oct. 2, 2007, now U.S. Pat. No. 8,114,815 which is a national stage application of International application No. PCT/JP2006/313471, filed Jul. 6, 2006.

TECHNICAL FIELD

The present invention relates to a herbicide composition capable of sustainedly exhibiting the effectiveness over a long period of time along with a decrease or prevention of any phytotoxicities and alleviation of the load on the environment.

BACKGROUND ART

It is known that, in known herbicides, herbicidal compounds comprising difluoromethanesulfonylanilide derivatives represented by

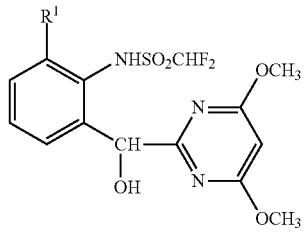

wherein $R^1$ is a hydrogen atom, an alkyl group, or an alkoxyalkyl group, or a salt thereof have high herbicidal effects at low doses on annual weeds such as *Echinochloa crus-galli, Cyperus difformis, Monochoria vaginalis, Ammannia multiflora* and the like, and perennial weeds, such as *Eleocharis acicularis, Sagittaria pygmaea, Sagittaria trifolia* and the like or, in particular, paddy weeds, and have broad herbicidal spectra (JP2000-44546A).

However, this herbicidal compound may be sometimes phytotoxic to rice, when applied under inappropriate conditions of weather, soil, control of water in the paddy field and the like or, when applied in excessive amounts unwillingly or accidentally.

In addition, an excessive application of this herbicidal compound may cause a risk of increased load on the environments due to flow-out to or residual amount in the environments including rivers, underground water, soils and others.

Therefore, the technologies are desired for employing herbicides capable of attaining increased safety to rice and sustainedly exhibiting the effectiveness over a long period of time along with alleviation of the load on the environment.

DISCLOSURE OF THE INVENTION

The object of the present invention is to provide a herbicide composition capable of sustainedly exhibiting the effectiveness of the herbicidal compound represented by the above-given general formula over a long period of time along with a decrease or prevention of any phytotoxicities and alleviation of the load on the environment.

As a result of the extensive investigations for solving the above problems, the inventors have arrived at a discovery that a contribution for the solution of the problems could be obtained with a herbicide composition containing the said herbicidal compound microencapsulated as the effective ingredient leading to establishment of the present invention on the base of this discovery.

Namely, the present invention provides: a herbicide composition characterized by containing a microencapsulated herbicidal compound selected from the group consisting of difluoromethanesulfonylanilide compounds represented by the general formula (I),

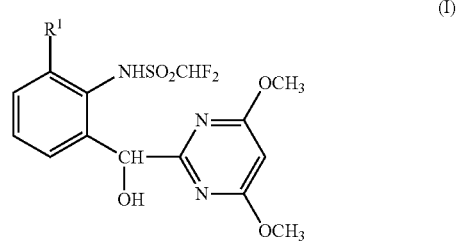

wherein $R^1$ is a hydrogen atom, an alkyl group, or an alkoxyalkyl group, and salts thereof; a herbicide composition characterized by containing the microencapsulated herbicidal compound mentioned above and a benzoic acid compound represented by the general formula (II),

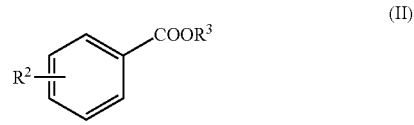

wherein $R^2$ is a hydrogen atom, an alkyl group having 1-15 carbon atoms, a hydroxyl group, a nitro group or an amino group, and $R^3$ is a hydrogen atom, an alkali metal atom or an alkyl group; a method for weeding in a paddy field characterized in that the herbicide composition is applied to the paddy field; and a method for the preparation of microcapsules for a herbicide composition characterized in that a first reactant solution comprising the above-mentioned herbicidal compound, a hydrophobic polyisocyanate and a hydrophobic solvent and a second reactant solution which is an aqueous solution containing a water-soluble polymer and a water-soluble active hydrogen-containing compound are mixed together and heated at 60 to 90° C. under high-speed agitation to form microcapsules having a coating of a polyurethane or a polyurea with the above-mentioned herbicidal compound sealed therein.

$R^1$ in the herbicidal compound of the above given general formula (I) used in the inventive composition is preferably a hydrogen atom, a linear or branched alkyl group having 1 to 6 carbon atoms, or a linear or branched alkoxyalkyl group having 2 to 6 carbon atoms in total. As the alkyl group, a methyl group, ethyl group, n-propyl group, isopropyl group, n-butyl group, isobutyl group, sec-butyl group, tert-butyl group, n-pentyl group, 1-methylbutyl group, n-hexyl group, and the like are preferable. As the alkoxyalkyl group, a methoxymethyl group, methoxyethyl group, ethoxyethyl group, 3-ethoxypropyl group, 1-methyl-3-methoxybutyl group, and the like are preferable.

In the case where the herbicidal compound is a salt, the salt is exemplified by a sodium salt, a potassium salt and the like.

(RS)-2'-(4,6-dimethoxypyrimidin-2-yl)hydroxymethyl-6'-methoxymethyl-1,1-difluoromethanesulfonylanilide (common name: "pyrimisulfan") is particularly preferable as the herbicidal compound.

Microcapsules with enclosure of the herbicidal compound represented by the general formula (I) can be produced, for example, by introducing a first reactant solution consisting of the aforementioned herbicidal compound, a hydrophobic polyisocyanate and a hydrophobic solvent into a second reactant solution consisting of an aqueous solution containing a water-soluble polymer and a water-soluble active hydrogen-containing compound and agitating the same at a high speed followed by heating to cause a reaction of the aforementioned hydrophobic polyisocyanate, aforementioned water-soluble polymer and aforementioned water-soluble active hydrogen-containing compound to form polyurethane- or polyurea-coated microcapsules with enclosure of the herbicidal compound.

In this forming method, it is also possible that the second reactant solution is contained in such a way that the first reactant solution and the aqueous solution of the water-soluble polymer are mixed together followed by separate addition of the active hydrogen-containing compound under gentle agitation to effect the reaction.

In this case, the hydrophobic polyisocyanate used in combination with the herbicidal compound in the first reactant solution includes, for example, a dimmer or trimer of an aliphatic or aromatic diisocyanate or a polymethylene polyphenyl polyisocyanate expressed by the formula

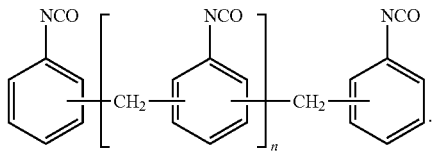

In the first reactant solution, the hydrophobic solvent for dissolving or suspending the herbicidal compound and the hydrophobic polyisocyanate includes ethers such as ethyl ether, dioxane, ethyleneglycol monoethyl ether, dipropyl ether, dibutyl ether, tetrahydrofuran and the like, aliphatic hydrocarbons such as normal paraffins, naphthenes, isoparaffins, kerosene, mineral oils and the like, aromatic hydrocarbons such as benzene, toluene, xylene, solvent naphtha, alkyl naphthalenes, 1-phenyl-1-xylyl ethane and the like, halogenated hydrocarbons such as dichloromethane, chloroform, carbon tetrachloride and the like, esters such as ethyl acetate, diisopropyl phthalate, dibutyl phthalate, dioctyl phthalate, dimethyl adipate and the like, vegetable oils such as soybean oil, rapeseed oil, cottonseed oil, castor oil and the like and so on, of which dichloromethane is particularly preferred.

Nextly, the water-soluble polymer used as the constituent of the second reactant solution includes, for example, polyacrylic acid and water-soluble salts thereof, polyethyleneglycols, poly(vinylpyrrolidone), poly(vinyl alcohol) and others.

Further, the water-soluble active hydrogen-containing compound to be contained in this second reactant solution includes, for example, hydroxyl compounds such as glycols and glycerol and amino compounds such as ethylenediamine. Water can also play a role as the active hydrogen-containing compound but need not be added separately because of the presence as the medium in the aqueous solutions.

The reaction between the first reactant solution and the second reactant solution can proceed by mixing them and heating the same at a temperature of 60 to 90° C. under high-speed agitation at a velocity of 1000 to 10000 rpm.

By this reaction, a polyurethane or a polyurea is formed to serve as the wall material when the active hydrogen-containing compound used is a hydroxyl compound or an amino compound or when water acts as the active hydrogen-containing compound, respectively.

Accordingly, the use proportion of the hydrophobic polyisocyanate in the first reactant solution and the water-soluble active hydrogen-containing compound and the water-soluble polymer in the second reactant solution each as the reactant should be selected in accordance with the stoichiometric amounts based on the reaction equations for the formation of a polyurethane or polyurea, respectively.

Further, the water-soluble polymer in the second reactant solution is selected within a concentration range of 1 to 5% by mass.

The reaction between the first reactant solution and the second reactant solution can be performed according to need in the presence of a water-soluble thickener such as xanthan gum, carboxymethylcellulose or a salt thereof, gum arabic, gelatin, dextrin and water-soluble starch, non-ionic surfactant such as sorbitan fatty acid esters, sucrose fatty acid esters, polyoxyethylene fatty acid esters, polyoxyethylene resinate esters, polyoxyethylene alkyl ethers, polyoxyethylene alkylphenyl ethers, polyoxyethylene-polyoxypropylene block copolymers, alkyl polyoxyethylene-polypropylene block copolymer ethers, polyoxyalkylene styrylphenyl ethers, polyoxyethylene castor oils, hydrogenated polyoxyethylene castor oils and the like and anionic surfactant such as alkyl sulfate salts, alkylbenzene sulfonate salts, lignin sulfonate salts, alkylsulfosuccinate salts, naphthalene sulfonate salts, alkylnaphthalene sulfonate salts, salts of naphthalenesulfonic acid-formalin condensate, salts of alkylnaphthalene sulfonic acid-formalin condensate and the like. These additives can be added to the first reactant solution or to the second reactant solution or alternatively can be added to the first reactant solution and second reactant solution individually.

As to the thus obtained microcapsules of the present invention, while an average particle diameter thereof (mass median diameter) can be freely selected, the said particle diameter can be usually selected in the range of 0.1-50 μm or, preferably, 1-20 μm.

The benzoic acid compound used in the composition of the present invention is a compound represented by the general formula (II)

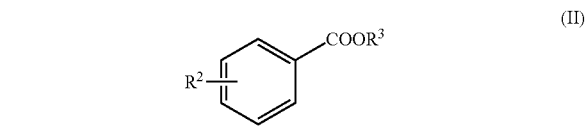

wherein $R^2$ is a hydrogen atom, an alkyl group having 1-15 carbon atoms, a hydroxyl group, a nitro group or an amino group, and $R^3$ is a hydrogen atom, an alkali metal atom or an alkyl group,
which is exemplified, for example, by p-alkylbenzoic acids such as p-ethylbenzoic acid, p-(n-propyl)benzoic acid, p-(n-butyl)benzoic acid, p-(tert-butyl)benzoic acid, p-(n-pentyl)benzoic acid, p-(n-hexyl)benzoic acid and the like, alkali metal salts thereof, alkyl esters thereof and the like. The alkali metal salts are preferably sodium salts such as, for example, sodium p-(tert-butyl)benzoate and the like. The alkyl esters include, for example, methyl p-(tert-butyl) benzoate and the like.

In the composition of the present invention, the use proportion of the herbicidal compound and the benzoic acid compound is selected in the range of, usually, 5:1 to 1:100 or, preferably, 2:1 to 1:50 by the mass ratio, though subject to adequate variations depending on the kind and growing periods of the objective crops, e.g., the transplanting time in rice and others.

In the composition of the present invention, it is also possible to use a blend of a herbicidal compound converted into microcapsules and the herbicidal compound before conversion into microcapsules.

It is possible according to need that the herbicide composition of the present invention may contain additional components usually used in pesticide formulations.

The additional components are exemplified by a carrier such as a solid carrier, liquid carrier and the like, a surfactant, a binder, a tackifier, a thickener, a colorant, a spreader, a sticker, an antifreezing agent, an anticaking agent, a disintegrator, a stabilizer and the like. In addition thereto, it is optional according to need that a preservative, a plant detritus and the like are used as the additional component. These additional components can be used singly or can be used as a combination of two kinds or more.

The above-mentioned additional components will be described. The solid carrier is exemplified, for example, by natural minerals such as quartz, clay, kaolinite, pyrophyllite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicate, starch, cellulose, a vegetable powder and the like; plastic carriers such as polyethylene, polypropylene, poly(vinylidene chloride) and the like; urea, hollow inorganic bodies, hollow plastic bodies, fumed silica (white carbon) and the like. These can be used singly or can be used as a combination of two kinds or more.

The liquid carrier includes, for example, alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol compounds such as propylene glycol ether and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, mineral oils and the like; aromatic hydrocarbons such as benzene, toluene, xylene, solvent naphtha, alkylnaphthalenes and the like; halogenated hydrocarbons such as dichloromethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water and the like. These can be used singly or can be used as a combination of two kinds or more.

The surfactant includes, for example, nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensates, polyoxyethylene-polyoxypropylene block copolymers, alkyl polyoxyethylene-polypropylene block copolymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate of naphthalene sulfonic acid, salts of formalin condensate of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylami-nopropylamine acetate salts, alkylamine salts including alkyltrimethylammonium chloride and alkyldimethylbenzalkonium chloride and the like; ampholytic surfactants such as amino acid or betaine surfactants and the like, and so on.

These surfactants can be used singly or can be used as a combination of two kinds or more.

The binder and tackifier include, for example, carboxymethylcellulose and a salt thereof, dextrin, water-soluble starch, xanthan gum, guar gum, sucrose, poly(vinylpyrrolidone), gum arabic, poly(vinyl alcohol), poly(vinyl acetate), sodium polyacrylate, poly(ethylene glycol) with an average molecular weight of 6000 to 20000, polyethylene oxide with an average molecular weight of 100000 to 5000000, phospholipid (for example, cephalin, lecithin and the like) and so on.

The thickener includes, for example, water-soluble polymers such as xanthan gum, guar gum, carboxymethylcellulose, poly(vinylpyrrolidone), a carboxyvinyl polymer, an acrylic polymer, a starch derivative and a polysaccharide; inorganic fine powders such as high-purity bentonite and fumed silica (white carbon), and the like.

The colorant includes, for example, inorganic pigments such as iron oxide, titanium oxide, and Prussian blue; organic dyes such as an alizarin dye, azo dye, and metal phthalocyanine dye, and the like.

The spreader includes, for example, a cellulose powder, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer consisting of polyhydric alcohol with dicarboxylic anhydride, a water-soluble salt of polystyrenesulfonic acid and the like.

The sticker includes, for example, paraffin, terpene, a polyamide resin, polyacrylate, polyoxyethylene, wax, polyvinyl alkyl ether, an alkylphenol-formalin condensate, a synthetic resin emulsion and the like.

The antifreezing agent includes, for example, polyhydric alcohols such as ethylene glycol, diethylene glycol, propylene glycol, glycerol and the like, and so on.

The anticaking agent includes, for example, polysaccharides such as starch, alginic acid, mannose, galactose and the like; poly(vinylpyrrolidone), fumed silica (white carbon), ester gum, a petroleum resin and the like.

The disintegrator includes, for example, sodium tripolyphosphate, sodium hexametaphosphate, metal stearates, a cellulose powder, dextrin, a methacrylate copolymer, poly (vinylpyrrolidone), a polyaminocarboxylic acid chelate compound, a sulfonated styrene-isobutylene-maleic anhydride copolymer, a starch-polyacrylonitrile graft copolymer and the like.

The stabilizer includes, for example, desiccants such as zeolite, calcined lime and magnesium oxide; antioxidants such as phenol compounds, amine compounds, sulfur compounds, phosphoric acid compounds and the like; ultraviolet absorbers such as salicylic acid compounds, benzophenone compounds and the like; and so on.

The preservative includes, for example, potassium sorbate, 1,2-benzothiazol-3-one and the like.

The plant detritus includes, for example, sawdust, coconut shell, corn cob, tobacco stalk and the like.

When the above-mentioned additional component is contained in the inventive herbicide composition, a content thereof is selected in the range of, on a mass basis, usually 5 to 95% or, preferably, 20 to 90% as a carrier, usually 0.1 to 30% or, preferably, 0.5 to 10% as a surfactant, and 0.1 to 30% or, preferably, 0.5 to 10% as other additives.

The herbicide composition of the present invention can be employed as prepared in any desired formulations including liquid formulations, emulsifiable concentrates, wettable powders, dust formulations, oil solutions, water dispersible granules, flowable, aqueous suspension concentrate formulations, emulsion waters, granules, jumbo formulations, suspo-emulsions, uniformly diffusible formulations and others.

When the herbicide composition of the present invention is in the form of granules, examples of granules include spherical, columnar, spindle-shaped and irregular ones and other forms having a particle diameter of from 0.3 mm to 10 mm.

The spherical granules have a particle diameter of, preferably, from 0.3 to 10 mm or, more preferably, from 0.3 mm to 3 mm.

The columnar granules preferably have a diameter of from 0.6 mm to 5 mm and a length of from 1 mm to 10 mm or, more preferably, a diameter of from 0.8 mm to 3 mm and a length of from 1.5 mm to 8 mm.

The spindle-shaped granules preferably have a breadth of from 0.3 mm to 3 mm and a length of from 1 mm to 10 mm.

When the herbicide composition of the present invention is a uniformly diffusible formulation, it is preferable that the particle size distribution thereof is such that the content of the granules having a particle diameter of 3 mm or larger is at least 80% by mass and that, when the herbicide composition of the present invention is put into water, the formulation floats on the water surface but the granules are disintegrated on the water surface within 30 minutes after putting.

During the formulation, the composition may be prepared as a mixture with at least one kind of other pesticides such as, for example, another herbicide, an insecticide, a fungicide, a plant growth regulator, a fertilizer and the like.

Any of the aforementioned formulations of the herbicide composition of the present invention can be wrapped with a water-soluble film so as, in this way, to contribute to labor saving in the application thereof along with an increase in the safety.

The preparation method of the inventive herbicide composition is not particularly limitative but usually includes the following methods.

A method in which a blend of the microencapsulated herbicidal compound and other starting materials is admixed with an appropriate volume of water for kneading followed by extrusion through a screen having an opening of a specified size for granulation and then drying.

A method in which the microencapsulated herbicidal compound and other starting materials are mixed with water or a suitable solvent to be uniformly suspended therein.

A method in which the microencapsulated herbicidal compound is blended with an appropriate carrier followed by drying and then blended with other starting materials.

BEST MODE FOR CARRYING OUT THE INVENTION

In the following, a description is given by way of Examples to show the best mode for carrying out the present invention. In each of the Examples, the "parts" indicating the amount used and the "%" indicating the proportion of contents are all based on the mass amount.

Example 1

Into 60 parts of dichloromethane were added 10 parts of pyrimisulfan and 9 parts of a polymethylene polyphenyl polyisocyanate (produced by Nippon Polyurethane Industry Co., product name "Millionate MR-100") and they were mixed together. This mixed solution was added to 100 parts of a 1% aqueous polyvinyl alcohol solution and agitated for 10 minutes with a dissolver (manufactured by Tokushu Kika Kogyo Co., product name "T.K. Robomics") at a revolution of 6000 rpm. Thereafter, microcapsules of pyrimisulfan with a polyurea film were obtained by gently agitating the mixed solution for 3 hours at 60° C. The microcapsules had an average particle diameter of 4.0 μm. Further, 15 parts of a sodium alkylnaphthalene sulfonate and 366 parts of a 2% aqueous xanthan gum solution were added thereto and they were uniformly blended together to give a microcapsule-containing aqueous suspension concentrate formulation (flowable) having 2% of pyrimisulfan.

Example 2

A 119 parts portion of the pyrimisulfan microcapsules obtained in Example 1 (containing 10 parts of pyrimisulfan) was admixed with 50 parts of p-(tert-butyl)benzoic acid, 15 parts of a sodium alkylnaphthalene sulfonate and 316 parts of a 2% aqueous xanthan gum solution and they were uniformly blended together to give a microcapsule-containing aqueous suspension concentrate formulation (flowable) having 2% of pyrimisulfan.

Example 3

Into 100 parts of dichloromethane were added 5 parts of pyrimisulfan and 5 parts of a polymethylene polyphenyl polyisocyanate (supra) and they were mixed together. This mixed solution was added to 250 parts of a 1% aqueous polyvinyl alcohol solution and agitated for 10 minutes with a dissolver (supra) at a revolution of 3000 rpm. Thereafter, microcapsules of pyrimisulfan with a polyurea film were obtained by gently agitating the mixed solution for 3 hours at 60° C. The microcapsules had an average particle diameter of 7.5 μm. Further, 50 parts of p-(tert-butyl)benzoic acid, 15 parts of a sodium alkylnaphthalene sulfonate and 175 parts of a 2% aqueous xanthan gum solution were added thereto and they were uniformly blended together to give a microcapsule-containing aqueous suspension concentrate formulation (flowable) having 1% of pyrimisulfan.

Example 4

Into 100 parts of dichloromethane were added 5 parts of pyrimisulfan and 0.5 part of a polymethylene polyphenyl polyisocyanate (supra) and they were mixed together. This mixed solution was added to 250 parts of a 1% aqueous polyvinyl alcohol solution and agitated for 10 minutes with a dissolver (supra) at a revolution of 3000 rpm. Thereafter, microcapsules of pyrimisulfan with a polyurea film were obtained by gently agitating the mixed solution for 3 hours at 60° C. The microcapsules had an average particle diameter of 12.3 μm. Further, 50 parts of p-(n-pentyl)benzoic acid, 15 parts of a sodium alkylnaphthalene sulfonate and 179.5 parts of a 2% aqueous xanthan gum solution were added thereto and they were uniformly blended together to give a microcapsule-containing aqueous suspension concentrate formulation (flowable) having 1% of pyrimisulfan.

Example 5

Into 50 parts of 1-phenyl-1-xylylethane (produced by Nippon Petrochemicals Co., product name "Hisol SAS-296") were added 5 parts of pyrimisulfan and 2.5 parts of a polymethylene polyphenyl polyisocyanate (supra) and they were mixed together. This mixed solution was added to 250 parts of a 1% aqueous polyvinyl alcohol solution and agitated for 10 minutes with a dissolver (supra) at a revolution of 3000 rpm. Thereafter, microcapsules of pyrimisulfan with a polyurea film were obtained by gently agitating the mixed solution for 3 hours at 60° C. The microcapsules had an average particle diameter of 16.0 μm. Further, 50 parts of p-(n-hexyl)benzoic acid, 15 parts of a sodium alkylnaphthalene sulfonate and 127.5 parts of a 2% aqueous xanthan gum solution were added thereto and they were uniformly blended together to give a microcapsule-containing aqueous suspension concentrate formulation (flowable) having 1% of pyrimisulfan.

Example 6

Into 100 parts of dichloromethane were added 5 parts of pyrimisulfan and 5 parts of a polymethylene polyphenyl polyisocyanate (supra) and they were mixed together. This mixed solution was added to 100 parts of a 3% aqueous gum arabic solution and agitated for 10 minutes with a dissolver (supra) at a revolution of 6000 rpm. Thereafter, a 10 parts portion of ethyleneglycol was added to the mixed solution followed by gentle agitation for 3 hours at 60° C. to obtain microcapsules of pyrimisulfan with a polyurethane film. The microcapsules had an average particle diameter of 5.6 μm. Further, 10 parts of n-butyl p-hydroxybenzoate, 15 parts of a sodium alkylnaphthalene sulfonate and 355 parts of a 2% aqueous xanthan gum solution were added thereto and they were uniformly blended together to give a microcapsule-containing aqueous suspension concentrate formulation (flowable) having 1% of pyrimisulfan.

Example 7

Into 100 parts of dichloromethane were added 5 parts of pyrimisulfan and 5 parts of a polymethylene polyphenyl polyisocyanate (supra) and they were mixed together. This mixed solution was added to 100 parts of a 3% aqueous gum arabic solution and agitated for 10 minutes with a dissolver (supra) at a revolution of 6000 rpm. Thereafter, a 10 parts portion of a 20% aqueous ethylenediamine solution was added to the mixed solution followed by gentle agitation for 3 hours at 60° C. to obtain microcapsules of pyrimisulfan with a polyurea film. The microcapsules had an average particle diameter of 5.5 μm. Further, 50 parts of n-butyl p-hydroxybenzoate, 15 parts of a sodium alkylnaphthalene sulfonate and 275 parts of a 2% aqueous xanthan gum solution were added thereto and they were uniformly blended together to give a microcapsule-containing aqueous suspension concentrate formulation (flowable) having 1% of pyrimisulfan.

Example 8

Into 100 parts of a 1% aqueous polyvinyl alcohol solution were added 5 parts of pyrimisulfan pulverized with a jet mill (manufactured by Seishin Enterprise Co., product name "SK Jet-O-Mill") and they were uniformly blended into a dispersion. A blend solution of 0.2 part of a polymethylene polyphenyl polyisocyanate (supra) and 40 parts of dichloromethane was added to the mixed solution and agitated for 10 minutes with a dissolver (supra) at a revolution of 3000 rpm. Thereafter, 1 part of ethyleneglycol was added to this mixed solution followed by gentle agitation for 3 hours at 60° C. to obtain microcapsules of pyrimisulfan with a polyurethane film. The microcapsules had an average particle diameter of 5.8 μm. Further, 50 parts of p-(n-hexyl)benzoic acid, 15 parts of a sodium alkylnaphthalene sulfonate and 328.8 parts of a 2% aqueous xanthan gum solution were added thereto and they were uniformly blended together to give a microcapsule-containing aqueous suspension concentrate formulation (flowable) having 1% of pyrimisulfan.

Example 9

A 119 parts portion of the pyrimisulfan microcapsules obtained in Example 1 (containing 10 parts of pyrimisulfan) was admixed with 20 parts of fentrazamide, 100 parts of p-(n-butyl)benzoic acid, 15 parts of a sodium alkylnaphthalene sulfonate and 246 parts of a 2% aqueous xanthan gum solution and they were uniformly blended together to give a microcapsule-containing aqueous suspension concentrate formulation (flowable) having 2% of pyrimisulfan and 4% of fentrazamide.

Example 10

A 89 parts portion of the pyrimisulfan microcapsules obtained in Example 1 (containing 7.5 parts of pyrimisulfan) was admixed with 2.5 parts of pyrimisulfan before conversion into microcapsules, 100 parts of p-(tert-butyl)benzoic acid, 15 parts of a sodium alkylnaphthalene sulfonate and 293.5 parts of a 2% aqueous xanthan gum solution and they were uniformly blended together to give a microcapsule-containing aqueous suspension concentrate formulation (flowable) having 2% of pyrimisulfan.

Example 11

A 12 parts portion of the pyrimisulfan microcapsules obtained in Example 1 (containing 1 part of pyrimisulfan) was admixed with 2 parts of an enzyme-modified dextrin, 1 part of sodium tripolyphosphate, 0.5 part of sodium dodecylbenzene sulfonate, 25 parts of bentonite and 69.5 parts of calcium carbonate and they were uniformly blended together. This mixture was admixed with an appropriate volume of water for kneading followed by extrusion granulation by using an extrusion granulator through a screen of 1.0 mm mesh opening diameter and particle size assorting was followed by drying at a material temperature of 60° C. and screening to give microcapsule-containing granules having 1% of pyrimisulfan.

Example 12

A 12 parts portion of the pyrimisulfan microcapsules obtained in Example 1 (containing 1 part of pyrimisulfan)

was admixed with 10 parts of p-(tert-butyl)benzoic acid, 2 parts of an enzyme-modified dextrin, 1 part of sodium tripolyphosphate, 0.5 part of sodium dodecylbenzene sulfonate, 25 parts of bentonite and 59.5 parts of calcium carbonate and they were uniformly blended together. This mixture was admixed with an appropriate volume of water for kneading followed by extrusion granulation by using an extrusion granulator through a screen of 1.0 mm mesh opening diameter and particle size assorting was followed by drying at a material temperature of 60° C. and screening to give microcapsule-containing granules having 1% of pyrimisulfan.

Example 13

A 12 parts portion of the pyrimisulfan microcapsules obtained in Example 1 (containing 1 part of pyrimisulfan) was admixed with 3 parts of benzobicyclon, 5 parts of p-(n-pentyl)benzoic acid, 2 parts of an enzyme-modified dextrin, 1 part of sodium tripolyphosphate, 0.5 part of sodium dodecylbenzene sulfonate, 25 parts of bentonite and 61.5 parts of calcium carbonate and they were uniformly blended together. This mixture was admixed with an appropriate volume of water for kneading followed by extrusion granulation by using an extrusion granulator through a screen of 1.0 mm mesh opening diameter and particle size assorting was followed by drying at a material temperature of 60° C. and screening to give microcapsules-containing granules having 1% of pyrimisulfan and 3% of benzobicyclon.

Example 14

A 9 parts portion of the pyrimisulfan microcapsules obtained in Example 1 (containing 0.8 part of pyrimisulfan) was admixed with 0.2 part of pyrimisulfan before conversion into microcapsules, 5 parts of p-(n-butyl)benzoic acid, 2 parts of an enzyme-modified dextrin, 1 part of sodium tripolyphosphate, 0.5 part of sodium dodecylbenzene sulfonate, 25 parts of bentonite and 64.8 parts of calcium carbonate and they were uniformly blended together. This mixture was admixed with an appropriate volume of water for kneading followed by extrusion granulation by using an extrusion granulator through a screen of 1.0 mm mesh opening diameter and particle size assorting was followed by drying at a material temperature of 60° C. and screening to give microcapsule-containing granules having 1% of pyrimisulfan.

Example 15

A 24 parts portion of the pyrimisulfan microcapsules obtained in Example 1 (containing 2 parts of pyrimisulfan) was admixed with 10 parts of fumed silica (white carbon) followed by drying at 60° C. to give a powder of microcapsules of pyrimisulfan. The same was admixed with 20 parts of n-butyl p-hydroxybenzoic acid, 3 parts of polyoxyethylene acetylene glycol, 2 parts of an enzyme-modified dextrin, 14 parts of hollow plastic bodies containing 85% of moisture content, 20 parts of anhydrous sodium sulfate and 26.9 parts of urea and they were uniformly blended together. This mixture was admixed with an appropriate volume of water for kneading followed by extrusion granulation by using an extrusion granulator through a screen of 5.0 mm mesh opening diameter and particle size assorting was followed by drying at a material temperature of 60° C. and screening to give a microcapsule-containing uniformly diffusible formulation having 2% of pyrimisulfan which had a diameter of from 3 mm to 7 mm and a length of from 3 mm to 20 mm.

The uniformly diffusible formulation consisted of granules, at least 99.0% by mass of which had a diameter of 3 mm or larger, and was put into water to observe that the formulation was floating on the water surface but the granules became disintegrated within 20 minutes after putting.

Example 16

A 24 parts portion of the pyrimisulfan microcapsules obtained in Example 1 (containing 2 parts of pyrimisulfan) was admixed with 20 parts of p-(tert-butyl)benzoic acid, 5 parts of sodium lauryl sulfate, 5 parts of a sodium alkylnaphthalene sulfonate-formalin condensate, 30 parts of diatomaceous earth and 35.9 parts of clay and they were uniformly blended together. This mixture was admixed with an appropriate volume of water for kneading followed by extrusion granulation by using an extrusion granulator through a screen of 0.7 mm mesh opening diameter and particle size assorting was followed by drying at a material temperature of 60° C. and screening to give microcapsule-containing water dispersible granules having 2% of pyrimisulfan.

Comparative Example 1

A uniform blend was obtained by mixing 2 parts of pyrimisulfan, 3 parts of sodium alkylnaphthalene sulfonate and 95 parts of a 2% aqueous xanthan gum solution followed by wet-process milling in a bead mill to give an aqueous suspension concentrate formulation (flowable) having 2% of pyrimisulfan.

Comparative Example 2

A uniform blend was obtained by mixing 1 part of pyrimisulfan, 2 parts of an enzyme-modified dextrin, 1 part of sodium tripolyphosphate, 0.5 part of sodium dodecylbenzene sulfonate, 25 parts of bentonite and 70.5 parts of calcium carbonate. This mixture was admixed with an appropriate volume of water for kneading followed by extrusion granulation by using an extrusion granulator through a screen of 1.0 mm mesh opening diameter and particle size assorting was followed by drying at a material temperature of 60° C. and screening to give granules having 1% of pyrimisulfan.

Test Example 1

Test for Dissolution In Water

Into a 15 cm diameter Petri dish of glass were taken, in a thermostatic chamber at 20° C., 700 ml of 3 degrees hard water to make up a water depth of 4 cm. An application treatment thereto was undertaken with each of the aqueous suspension concentrate formulations obtained in Examples 1, 2 and 10 and Comparative Example 1 each in an amount corresponding to 500 ml per 10 a (ares) and the granules obtained in Examples 11, 12 and 14 and Comparative Example 2 each in an amount corresponding to 1 kg per 10 a (ares). After 1, 3, 7 and 14 days from the treatment, the water was taken and analyzed by the HPLC to determine the concentration of pyrimisulfan in water from which the proportions of the dissolved amount relative to the amount of actual application were obtained. The results are shown in Table 1.

TABLE 1

|  |  | Dissolved proportion of pyrimisulfan, % | | | |
|---|---|---|---|---|---|
|  |  | After 1 day | After 3 days | After 7 days | After 14 days |
| Example 1 | Flowable | 24 | 47 | 65 | 82 |
| Example 2 | Flowable | 18 | 41 | 65 | 76 |
| Example 10 | Flowable | 41 | 66 | 84 | 100 |
| Example 11 | Granules | 41 | 59 | 65 | 65 |
| Example 12 | Granules | 12 | 59 | 71 | 76 |
| Example 14 | Granules | 29 | 60 | 76 | 83 |
| Comparative Example 1 | Flowable | 100 | 100 | 100 | 100 |

TABLE 1-continued

|  |  | Dissolved proportion of pyrimisulfan, % | | | |
|---|---|---|---|---|---|
|  |  | After 1 day | After 3 days | After 7 days | After 14 days |
| Comparative Example 2 | Granules | 100 | 100 | 100 | 100 |

It is understood from Table 1 that pyrimisulfan is imparted with sustained releasability indicating a low-level shift of the dissolved proportion as compared Examples with Comparative Examples.

Testing Example 2

Test for Biological Effects: Paddy Rice

Plastic pots of 100 cm2 were each filled with paddy field soil and, after watering and scraping, sowing was conducted with respective seeds of Echinochloa oryzoides, Monochoria vaginalis and Scirpus juncoides into a depth of 0.5 cm. Further, two paddy rice plants at the two-leaves period were transplanted in a transplanting depth of 2 cm followed by water pooling in a water depth of 5 cm. In the next day to follow transplanting, each of the herbicide compositions obtained in Examples 1, 2, 10, 11, 12 and 14 and Comparative Examples 1 and 2 was taken by weighing and uniformly applied to the plastic pot in an amount corresponding to 5 g/10 a (ares) of the effective ingredient. These plants in the plastic pots were grown in the greenhouse and, after 28 days, subjected to estimation of the herbicidal effectiveness and the extent of the phytotoxity according to the evaluation criteria of Table 2. The results are shown in Table 3.

TABLE 2

| Index | Evaluation criteria |
|---|---|
| 5 | At least 90% herbicidal (weed-controlling) effect or phytotoxicity |
| At least 4 and less than 5 | At least 70% and less than 90% herbicidal effect or phytotoxicity |
| At least 3 and less than 4 | At least 50% and less than 70% herbicidal effect or phytotoxicity |
| At least 2 and less than 3 | At least 30% and less than 50% herbicidal effect or phytotoxicity |
| At least 1 and less than 2 | At least 10% and less than 30% herbicidal effect or phytotoxicity |
| At least 0 and less than 1 | Less than 10% herbicidal effect or phytotoxicity |

TABLE 3

|  |  | Herbicidal effect | | | |
|---|---|---|---|---|---|
|  |  | Echinochloa oryzoides | Monochoria vaginalis | Scirpus juncoides | Phytotoxicity Paddy rice |
| Example 1 | Flowable | 5 | 5 | 5 | 0.5 |
| Example 2 | Flowable | 5 | 5 | 5 | 0 |
| Example 10 | Flowable | 5 | 5 | 5 | 0 |
| Example 11 | Granules | 5 | 5 | 5 | 0.5 |
| Example 12 | Granules | 5 | 5 | 5 | 0 |
| Example 14 | Granules | 5 | 5 | 5 | 0 |
| Comparative Example 1 | Flowable | 5 | 5 | 5 | 1.5 |
| Comparative Example 2 | Granules | 5 | 5 | 5 | 1.5 |

As is understood from Table 3, the herbicide compositions of the Examples exhibit excellent herbicidal effects almost without any phytotoxicities against paddy rice while, in contrast thereto, considerable phytotoxicities were noted in Comparative Examples against paddy rice.

Testing Example 3

Test for Biological Effects: Tests for Residual Effects

Watering and scraping of 200 cm$^2$ plastic pots filled with a paddy field soil were followed by the addition of water to make up a water depth of 5 cm and treatment was conducted by applying one of the herbicide compositions obtained in Examples 1, 2, 10, 11, 12 and 14 and Comparative Examples 1 and 2 taken by weighing in an amount of 2.5 g/10 a (ares) as the effective ingredient. The treatment was immediately followed by 3 days of dewatering at a water-depth decreasing rate of 2 cm a day by causing water leakage from the bottom of the plastic pot. The water leakage was followed by the addition of water from above the plastic pot to make up a water depth of 5 cm. Immediately after the treatment and 20 days and 40 days after the treatment, seeds of *Echinochloa oryzoides, Monochoria vaginalis* and *Scirpus juncoides* were sowed and growth of the weeds was observed after 30 days from sowing. The evaluation criteria of the herbicidal effects were as those in Testing Example 2. The results of the evaluation are shown in Table 4.

TABLE 4

| | | Herbicidal effects | | | | | | | |
|---|---|---|---|---|---|---|---|---|---|
| | | *Echinochloa oryzoides* | | | *Monochoria vaginalis* | | | *Scirpus juncoides* | | |
| | | 0 day | 20 days | 40 days | 0 day | 20 days | 40 days | 0 day | 20 days | 40 days |
| Example 1 | Flowable | 4.4 | 4.3 | 3.8 | 4.7 | 4.8 | 4.3 | 4.7 | 4.8 | 4.7 |
| Example 2 | Flowable | 4.4 | 4.4 | 3.8 | 4.7 | 4.8 | 4.5 | 4.8 | 4.9 | 4.8 |
| Example 10 | Flowable | 4.4 | 4.4 | 4 | 4.8 | 4.8 | 4.5 | 4.9 | 4.9 | 4.8 |
| Example 11 | Granules | 4.3 | 4.3 | 3.8 | 4.7 | 4.8 | 4.3 | 4.7 | 4.9 | 4.8 |
| Example 12 | Granules | 4.3 | 4.3 | 3.8 | 4.7 | 4.8 | 4.5 | 4.8 | 4.9 | 4.7 |
| Example 14 | Granules | 4.3 | 4.3 | 4 | 4.8 | 4.9 | 4.5 | 4.9 | 4.9 | 4.8 |
| Comparative Example 1 | Flowable | 4.4 | 3.3 | 3 | 4.8 | 4.3 | 3 | 4.8 | 4.8 | 3.7 |
| Comparative Example 2 | Granules | 4.3 | 3.5 | 3 | 4.8 | 4.3 | 3 | 4.8 | 4.8 | 3.7 |

As is understood from Table 4, the herbicide compositions of the Examples exhibit superior residual effects as compared with Comparative Examples.

INDUSTRIAL APPLICABILITY

The herbicide composition of the present invention is adequately imparted with sustained releasability of the herbicidal compound in respect of dissolution into water so as to exhibit the phytotoxicities of the herbicidal compound over a long period of time along with a decrease of the environmental load due to the decreased releasing rate of the herbicidal compounds to the environment and also decrease or prevention of the phytotoxicities against the objective crops so that remarkable advantages can be obtained thereby.

Furthermore, the herbicide composition of the present invention is particularly useful as a herbicide for rice or for paddy fields because of alleviation or prevention of the syndrome of phytotoxicities in the objective crops along with sustainability of the effects over a long period of time.

The invention claimed is:

1. A granular herbicide composition comprising a microencapsulated herbicidal difluoromethanesulfonylanilide compound represented by the formula:

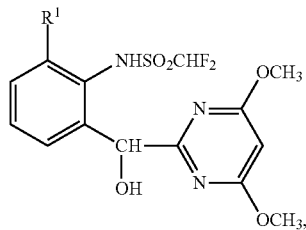

wherein $R^1$ is a methoxymethyl group, or a salt thereof,
  wherein the microencapsulated herbicidal compound has an average particle diameter of 0.1-50 μm,
  wherein the granular herbicide composition is a uniformly diffusible formulation having a granule particle size distribution, wherein at least 80% of the granules by mass have a diameter of 3 mm or larger and a property of floating on a water surface but disintegrating over the water surface within 30 minutes.

2. A method for weeding in a paddy field, comprising applying the granular herbicide composition according to claim 1 to a paddy field,
  wherein the granules disintegrate within 30 minutes of applying the composition to the paddy field.

* * * * *